US00RE39896E

(19) United States
(12) Reissued Patent
Arnold et al.

(10) Patent Number: US RE39,896 E
(45) Date of Reissued Patent: Oct. 23, 2007

(54) DISPOSABLE EYE PATCH AND METHOD OF MANUFACTURING A DISPOSABLE EYE PATCH

(75) Inventors: Nancy L. Arnold, Andover, MN (US); Jeffrey M. Stein, Waconia, MN (US)

(73) Assignee: GPT Glendale, Inc., Smithfield, RI (US)

(21) Appl. No.: 10/716,246

(22) Filed: Dec. 23, 2003

Related U.S. Patent Documents

Reissue of:
(64) Patent No.: 6,320,094
Issued: Nov. 20, 2001
Appl. No.: 09/663,382
Filed: Sep. 15, 2000

(51) Int. Cl.
*A61F 13/00* (2006.01)

(52) U.S. Cl. ..... 602/54; 128/858; 604/294; 604/307; 602/74

(58) Field of Classification Search ..... 602/54, 602/74; 128/858; 604/294, 307
See application file for complete search history.

(56) References Cited

U.S. PATENT DOCUMENTS

| | | | |
|---|---|---|---|
| 1,161,321 | A | 11/1915 | Lush |
| 1,275,127 | A | 8/1918 | Campbell |
| 2,165,668 | A | 7/1939 | Vaccaro |
| 2,283,752 | A | 5/1942 | Gonsett |
| 2,527,947 | A | 10/1950 | Loos |
| 2,572,638 | A | 10/1951 | Loos |
| 2,643,382 | A | 6/1953 | McLeod |
| 3,068,863 | A | 12/1962 | Bowman |
| 3,092,103 | A | 6/1963 | Mower |
| 3,121,021 | A | 2/1964 | Copeland |
| 3,339,206 | A | 9/1967 | Daley |
| 3,521,630 | A | 7/1970 | Westberg et al. |
| 3,814,095 | A | 6/1974 | Lubens |
| 3,908,645 | A | 9/1975 | Sandvig |
| 4,022,203 | A | 5/1977 | Ackley |
| 4,117,842 | A | 10/1978 | Hutchins |
| 4,122,847 | A | 10/1978 | Craig |
| 4,134,401 | A | 1/1979 | Galician |
| 4,331,136 | A | 5/1982 | Russell et al. |

(Continued)

FOREIGN PATENT DOCUMENTS

| | | |
|---|---|---|
| DE | 24 29 989 | 6/1974 |
| WO | WO 93/06678 | 4/1993 |

OTHER PUBLICATIONS

Pellegrini et al., U.S. Appl. No. 09/988,335, filed Nov. 19, 2001.

ABSORBING, vol. 2, Issue 2, Oct. 1994.

GPT Glendale, Inc., Patient Care Derm–Aid™ Disposables.

GPT Glendale, Inc. Non–Laser Disposable Derm Aid™ Eye Shield.

*Primary Examiner*—Lalita M. Hamilton
(74) *Attorney, Agent, or Firm*—Oliff & Berridge, PLC

(57) ABSTRACT

A disposable eye patch includes a first sheet member, a second sheet member smaller than the first sheet member, and an adhesive layer applied to one side of the first sheet member. One portion of the adhesive layer bonds the first and second sheet members together, and another portion of the adhesive layer adheres to the tissue surrounding an eye when the eye patch is applied to a patient. A release layer may be provided to cover the exposed portion of the adhesive layer, and may be peeled off prior to the use of the eye patch. The release layer and a plurality of eye patches may be provided in the form of a dispenser roll assembly. In a method of manufacturing the disposable eye patch, the first and second sheet members may both be formed from a sheet material having an adhesive layer, and then the first and second sheet members may be adhered together with the adhesive layer on one of the sheet members contacting the adhesive layer on the other one of the sheet members.

60 Claims, 4 Drawing Sheets

U.S. PATENT DOCUMENTS

| | | | |
|---|---|---|---|
| 4,339,035 | A | 7/1982 | Marcus et al. |
| 4,473,370 | A | 9/1984 | Weiss |
| 4,581,877 | A | 4/1986 | Wilber |
| 4,635,625 | A | 1/1987 | Teeple |
| 4,682,371 | A | 7/1987 | Heltman |
| 4,701,962 | A | 10/1987 | Simon |
| 4,709,695 | A | 12/1987 | Kohn et al. |
| 4,719,909 | A | 1/1988 | Micchia et al. |
| 4,790,031 | A | 12/1988 | Duerer |
| 4,793,002 | A | 12/1988 | Simon |
| 4,793,003 | A | 12/1988 | Riedel et al. |
| 4,862,902 | A | 9/1989 | Goffman |
| 4,867,146 | A | 9/1989 | Krupnick et al. |
| 4,944,040 | A | 7/1990 | Riedel et al. |
| 4,951,658 | A | 8/1990 | Morgan et al. |
| 4,969,472 | A | 11/1990 | Langley et al. |
| 4,995,114 | A | 2/1991 | Price, Jr. |
| 5,004,333 | A | 4/1991 | Bruhl, Jr. |
| 5,180,360 | A | 1/1993 | Rhame, Jr. |
| 5,190,810 | A | 3/1993 | Kirschbaum et al. |
| 5,191,897 | A | 3/1993 | Meshel |
| 5,209,718 | A | 5/1993 | McDaniel |
| 5,309,925 | A | 5/1994 | Policastro |
| 5,469,864 | A | 11/1995 | Rosenblatt |
| 5,524,642 | A | 6/1996 | Rosenblatt |
| 5,740,550 | A | 4/1998 | Yavitz |
| 5,769,806 | A | 6/1998 | Radow |
| 5,782,672 | A | 7/1998 | Woodley |
| 5,887,590 | A | 3/1999 | Price |
| 5,918,600 | A | 7/1999 | Durette |
| 5,970,515 | A | 10/1999 | Fishbaugh |
| 5,980,497 | A | 11/1999 | Yavitz |
| D421,124 | S | 2/2000 | Yavitz |
| D425,623 | S | 5/2000 | Funk |
| 6,090,060 | A | 7/2000 | Radow |
| 6,098,628 | A | 8/2000 | Funk |
| 6,131,208 | A | 10/2000 | Banks |
| 6,149,615 | A | 11/2000 | Gallamore |
| D446,307 | S | 8/2001 | Bassett |

DISPOSABLE EYE PATCH AND METHOD OF MANUFACTURING A DISPOSABLE EYE PATCH

Matter enclosed in heavy brackets [ ] appears in the original patent but forms no part of this reissue specification; matter printed in italics indicates the additions made by reissue.

BACKGROUND OF THE INVENTION

1. Field of Invention

This invention relates to a disposable eye patch. In particular, this invention relates to a disposable eye patch used during surgical and/or professional facial care procedures.

2. Description of Related Art

Cosmetic surgical procedures (e.g., plastic surgery) and professional facial care procedures are becoming increasingly popular. In some cases, patients request such procedures for facial parts such as the nose bridge, forehead, temples, and areas immediately surrounding the eyes. During surgical or other procedures to such facial parts, since the procedures often require very delicate and detailed work, doctors and other professionals must have access to as much unobstructed area as possible. At the same time, the doctors or other professionals need to avoid damaging the patient's eyes by various surgical, medial and cosmetic items, such as abrasion systems, chemicals, air jets, air streams, liquids, medicines, medicine applicators, surgical tools (e.g., scalpels, hemostats, needles, etc.) and other devices.

Therefore, the patient's eyes are often covered by materials such as a surgical tape and gauze while a surgical or facial care procedure is being performed. However, there is a need for more complete access to areas around the patient's eyes and for more reliable protection methods and devices.

U.S. Pat. No. 4,682,371 to Heltman discloses a protective eye patch. This eye patch has several adhesive tabs for securing the eye patch on the patient's eye. However, since the tabs do not entirely adhere the edge of the eye patch, there is a possibility that liquids or medicines may enter a patient's eye covered by this eye patch.

U.S. Pat. No. 3,068,863 to Bowman discloses another type of protective eye patch. This eye patch is designed to keep the eye closed. However, since this patch is adhered onto the patients eyelid and surrounding eye tissues, this eye patch is not comfortable to wear.

U.S. Pat. No. 3,092,103 to Mower provides an eye patch that has a cushion material on an edge of the eye patch, and allows a patient's eye to move and/or open underneath the eye patch. Because of its large size, this patch is not suitable for many surgical and facial care procedures.

U.S. Pat. No. 4,867,146 to Krupnick et al. discloses an eye patch for preventing opening of an eye and preventing corneal abrasion. This eye patch has adhesive areas around the patch and part of a center part of the eye patch. However, because of the adhesive areas in the center part, it is uncomfortable for the patient to wear the eye patch for a long time. In fact, it is designed for use on an anesthetized patient.

U.S. Pat. No. 5,180,360 to Rhame, Jr. discloses an oval shaped eye patch with a thick inner foam patch or adjustable bladder for adjusting pressure against an eyelid. This patch is quite large, being designed to attach to the outside of the eye socket, and covers some areas of the face that may need to be accessed for some surgical or facial care procedures.

SUMMARY OF THE INVENTION

This invention provides a small size disposable eye patch that allows doctors or other professionals full access to areas around the eyes for surgery and facial care procedures and is comfortable for the patient to wear.

A disposable eye patch according to the invention includes a first sheet member, a second sheet member smaller than the first sheet member, and an adhesive layer applied to one side of at least the first sheet member. One portion of the adhesive layer bonds the first and second sheet members together, and another portion of the adhesive layer adheres to the tissue surrounding an eye when the eye patch is applied to a patient. A release layer may be provided to cover the exposed portion of the adhesive layer, and peeled off prior to use of the eye patch.

The first and/or second sheet member may be made of biocompatible foamed plastic material, such as foamed PVC (polyvinyl chloride) or the like. The first adhesive layer is preferably pressure-sensitive, latex-free and hypoallergenic. The first and second sheet members preferably have the same thickness, and are made of the same material.

In a method of manufacturing the disposable eye patch, the first and second sheet members may both be formed from a sheet material having an adhesive layer, and then the first and second sheet members may be adhered together with the adhesive layer on one of the sheet members contacting the adhesive layer on the other one of the sheet members.

These and other features and advantages of this invention are described in or are apparent from the following description of exemplary embodiments.

BRIEF DESCRIPTION OF THE DRAWINGS

An embodiment of the invention will now be described with reference to the accompanying drawings, in which.

DETAILED DESCRIPTION OF PREFERRED EMBODIMENTS

Figure 1:
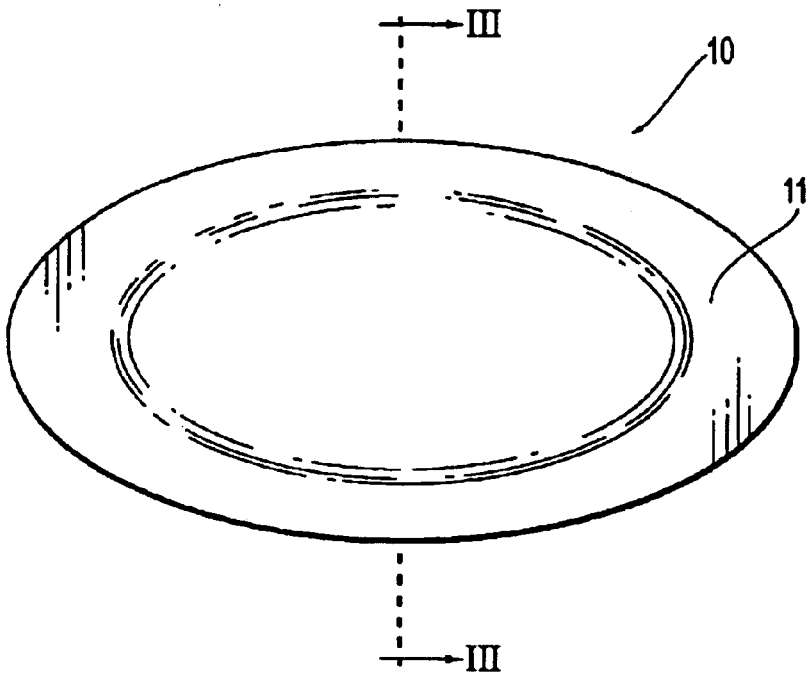
FIG. 1 is a top view of a disposable eye patch.
Figure 2:
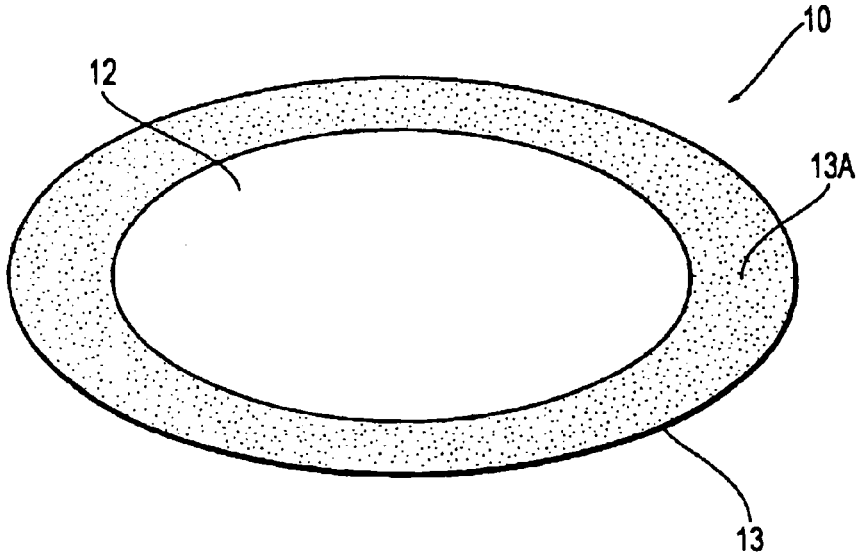
FIG. 2 is a bottom view of the disposable eye patch of FIG. 1.

As shown in FIGS. 1 and 2, a disposable eye patch 10 includes a first sheet member 11 and a second sheet member 12. These first and second sheet members are preferably oval in shape, although other shapes, such as a teardrop shape or the like, are also possible. "Oval" in the context of this application includes elliptical, oblong, and egg shapes. The first sheet member 11 is preferably made of biocompatible foamed plastic material. The second sheet member 12 is also preferably made of biocompatible foamed plastic material.

The eye patch 10 includes a first adhesive layer 13 on one side of the first sheet member 11 for adhering the eye patch 10 onto the tissue surrounding the patient's eye and for adhering the first sheet member 11 to the second sheet member 12. This first adhesive layer 13 may have a plan view size approximately equal to the plan view size of the first sheet member 11 and is preferably made of a pressure-sensitive adhesive (i.e., it may acquire greater adhesion with an adjacent surface as pressure between that surface and the adhesive is increased), preferably a latex-free and hypoallergenic material. The adhesion of the adhesive layer 13 should be strong enough to adhere reliably to the skin but weak enough to be easily removed from the skin after use.

Figure 3:
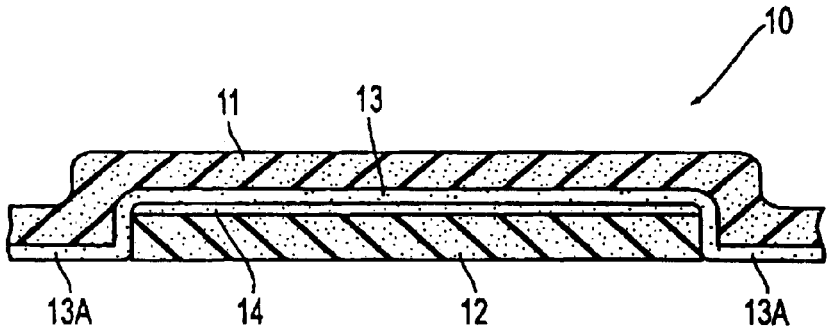
FIG. 3 is a cross-sectional view of the disposable eye patch of FIG. 1.

As shown in FIG. 3, the eye patch 10 may also include a second adhesive layer 14 between the second sheet member 12 and the first adhesive layer 13. The second adhesive layer 14 is not essential, but improves adhesion of the second sheet member 12 to the first sheet member 11. The second adhesive layer 14 may have a plan view size equal to the plan view size of the second sheet member 12. The second adhesive layer 14 may be made of the same material as the first adhesive layer 13.

The first sheet member 11 has a size that sufficiently covers the patient's eye and eyelid when applied. For instance, for an adult patient, the first sheet member 11 preferably has a length of from about 40 mm to about 60 mm, more preferably about 50 mm, and a width from about 20 mm to about 35 mm, more preferably about 28 mm. The second sheet member 12 preferably joins the first sheet member 11 at a central portion of the first adhesive layer 13 as shown in FIG. 2.

Having the above-described length and width allows the eye patch 10 to fit within the eye socket of a patient, and thus maximizes the facial area accessible to a doctor or other professional. The part of the eye patch 10 that contacts most of the patient's eyelid is free of exposed adhesive. This is more comfortable to the wearer, and allows the eye and eyelid to slightly move underneath the eye patch 10. Specifically, the side of the sheet member 12 facing the eye and eyelid is free of adhesive. This also prevents needless pain or discomfort when the eye patch is removed after use.

A peripheral portion 13A of the first adhesive layer 13, which is not overlapped by the second sheet member 12, should be large enough to provide sufficient adhesion of the eye patch 10 to the area of the face surrounding the eye. For example, the peripheral portion 13A may have a width of approximately 5 mm.

The first sheet member 11 and the second sheet member 12 each preferably have a thickness in a range of from about 0.1 mm to about 5 mm, more preferably from about 0.1 mm to about 2 mm, and even more preferably from 0.5 mm. The appropriate thickness may vary depending upon the type of procedure for which the eye patch is intended to be used, but in general, a thinner eye patch is desired to reduce the bulkiness of the eye patch 10 and increase the comfort of the patient. For example, for a so-called microdermabrasion process, in which aluminum-oxide crystals or the like are discharged from a wand onto a patient's face, an eye patch 10 with a first sheet member 12 with a thickness of about 0.5 mm and a second sheet member 12 with a thickness of about 0.5 mm and effectively protects the eyes.

The color of the eye patch 10 may be the natural color of the foamed plastic material, such as off-white, cream, or the like, or any other desired color such as beige, gray, black, fluorescent green, etc.

Figure 4:
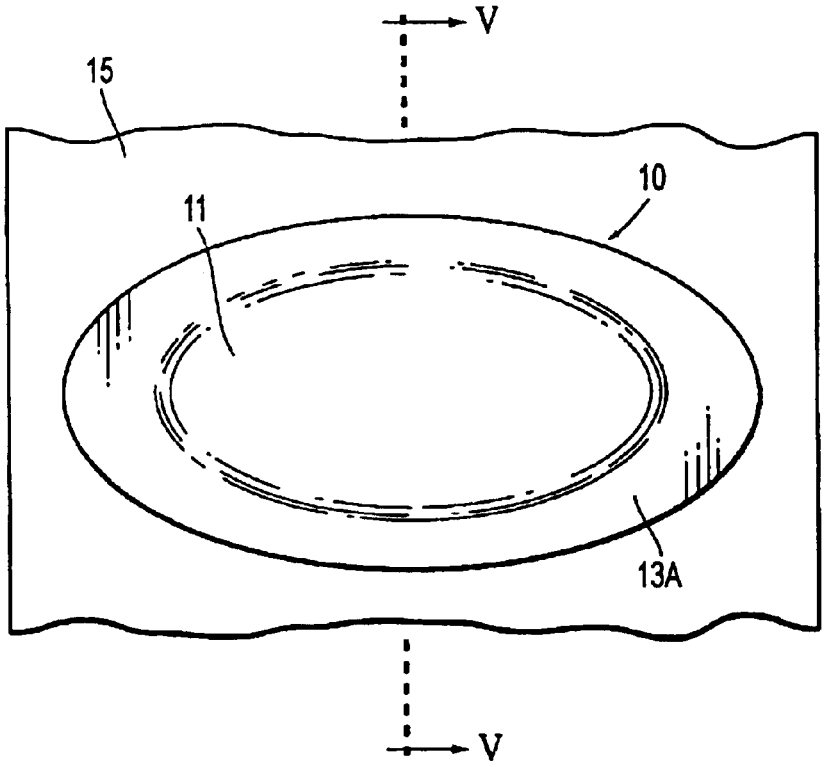
FIG. 4 is a top view of the disposable eye patch of FIG. 1 mounted on a release layer.
Figure 5:
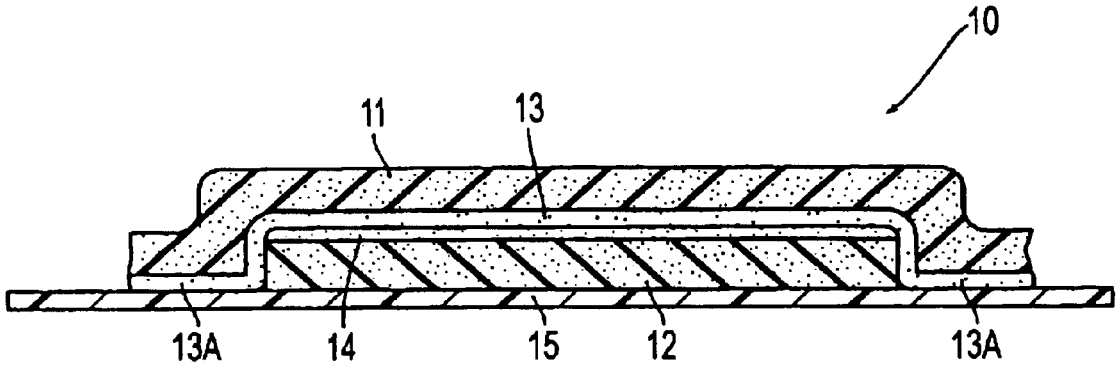
FIG. 5 is a cross-sectional view of the disposable eye patch and the release layer of FIG. 4.

As shown in FIGS. 4 and 5, to prevent the peripheral portion 13A of the adhesive layer 13 and the eye-contacting side of the second sheet member 12 of the eye patch 10 from being contaminated, the peripheral portion 13A of the adhesive layer 13 may be attached to a release layer 15, which is removed prior to use of the eye patch 10. The release layer 15 may, for example, be a waxed paper, plastic film or the like.

Figure 6:
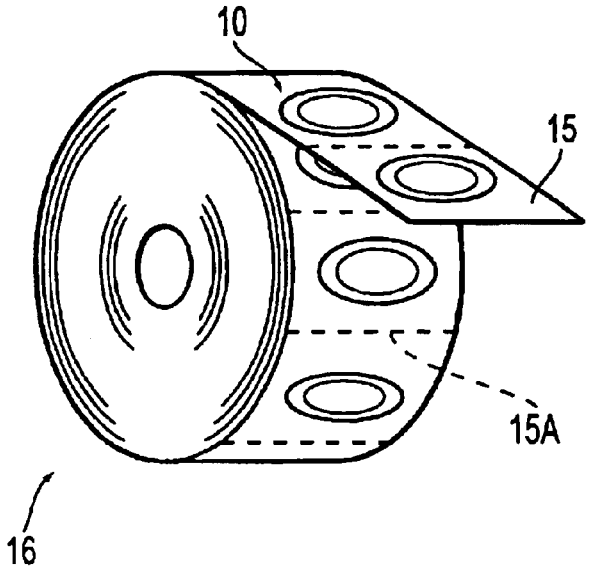
FIG. 6 is a perspective view of the eye patch of FIG. 1 provided on a dispenser roll.

The release layer 15 may be a continuous strip provided in the form of a dispenser roll 16, as shown in FIG. 6, with eye patches 10 provided at a predetermined spacing. This dispenser roll 16 may be provided in a dispenser box (not shown) and fed through a slot or the like provided in the box. The release layer 15 may have serrations 15A in between the eye patches 10 to facilitate separation into discrete units. Providing the release layer 15 and eye patches in the form of the dispenser roll 16 allows convenient dispensing and helps keep the eye patches 10 clean, since the eye patches 10 are not exposed until use.

When the eye patch 10 is to be applied to a patient, the release layer 15 is first peeled off from the disposable eye patch 10. When the release layer 15 has been removed, the peripheral portion 13A of the first adhesive layer 13 is exposed. The eye patch 10 is then positioned over the patient's closed eye and eyelid, and the edge of the eye patch 10 is gently pressed to seal the peripheral portion 13A of the adhesive layer 13 to the facial tissue surrounding the patient's eye and eyelid. After use, the eye patch 10 is gently peeled away from the eye and eyelid.

Figure 7:
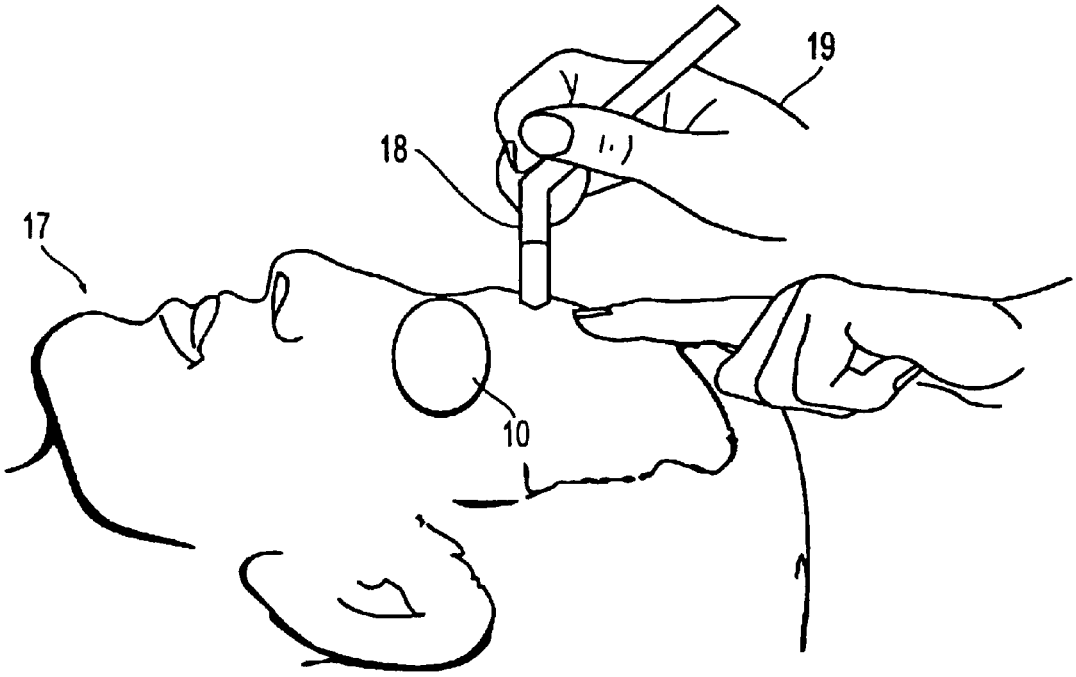
FIG. 7 shows the disposable eye patch of FIG. 1 being used during a facial care procedure.

FIG. 7 shows an example of a patient 17 wearing the disposable eye patch 10 and tissues around the patient's eye. During this treatment, the tissue areas directly around the patient's eye are exposed and accessible to the doctor or therapist 19 using a tool 18, while the eye is protected by the eye patch 10.

A method of manufacturing the eye patch 10 will now be described. First, a sheet material is provided having an adhesive layer coated on one side thereof. The first sheet member 11 and the second sheet member 12 are formed from the sheet material, e.g., by stamping, cutting or the like. Then the first sheet member 11 and the second sheet member 12 are positioned properly with respect to each other and pressed together, with their adhesive-coated surfaces facing each other and coming into contact. Finally, the eye patch 10 is attached to release layer 15, with the exposed peripheral portion 13A of the adhesive on the first sheet member 11 contacting the release layer 15.

This method for manufacturing is not limited to the above-described order of steps. For example, the second sheet member 12 can be cut first, and then adhered to the sheet material. The first sheet member 11 can then be cut in the predetermined shape, thus forming the eye patch 10.

The above-mentioned method of manufacturing an eye patch is relatively fast and easy, since it basically involves only one or two cutting steps and a press-together step, and economical since the only materials needed are a single type of adhesive-coated sheet and a release layer material.

While the invention has been described in conjunction with specific embodiments described above, many equivalent alternatives, modifications and variations will become apparent to those skilled in the art once given this disclosure. Accordingly, the preferred embodiments of the invention as set forth above are considered to be illustrative and not limiting. Various changes to the described embodiments may be made without departing from the spirit and scope of the invention. For example, although the illustrated embodiment has two adhesive layers 13 and 14, it is also possible to have only one adhesive layer. As another example, although the eye patch preferably has a generally oval shape, a tab (not shown) may be provided on an edge of the eye patch 10 to allow easy gripping and peeling of the eye patch 10 from the eye and eyelid after use. Such a tab should be large enough for fingers to grip, but otherwise as small as possible to leave as much facial area exposed as possible.

What is claimed is:

1. A disposable eye patch for covering a human eye, comprising:

a first sheet member sized to fit entirely inside an eye socket;

a second sheet member smaller than the first sheet member; and a first adhesive layer applied over substantially an entire surface of one side of the first sheet member, the first sheet member being attached to the second sheet member by a central portion of the first adhesive layer, and the second sheet member not overlapping a peripheral portion of the first adhesive layer.

2. The disposable eye patch according to claim 1, further comprising a release layer attached to the peripheral portion of the first adhesive layer.

3. The disposable eye patch according to claim 1, wherein at least one of the first sheet member and the second sheet member is made of biocompatible foamed plastic material.

4. The disposable eye patch according to claim 1, wherein the first sheet member and the second sheet member are made of a same material.

5. The disposable eye patch according to claim 1, wherein the first adhesive layer comprises a pressure-sensitive adhesive.

6. The disposable eye patch according to claim 1, further comprising a second adhesive layer between the first adhesive layer and the second sheet member.

7. The disposable eye patch according to claim 1, wherein a width of the first sheet member is in a range of from about 20 mm to about 35 mm, and a length of the first sheet member is in a range of from about 40 mm to about 60 mm.

8. A method of protecting a patients eye during treatment of an adjacent portion of the patient's face, comprising adhering a disposable eye patch according to claim 1 over said eye and entirely within a corresponding eye socket of said patient.

9. A dispenser roll assembly, comprising:

an elongate release layer coiled into a roll;

a plurality of disposable eye patches according to claim 1 arranged along the release layer and releasably attached to the release layer by the first adhesive layer.

10. A disposable eye patch comprising:

a first sheet member having a first thickness;

a second sheet member smaller than the first sheet member having a second thickness substantially equal to the first thickness;

a first adhesive layer applied over substantially an entire surface of one side of the first sheet member, the first sheet member being attached to the second sheet member by a central portion of the first adhesive layer, and the second sheet member not overlapping a peripheral portion of the first adhesive layer.

11. The disposable eye patch according to claim 10, wherein the first and second thicknesses are each in a range of from about 0.1 mm to about 5 mm.

12. The disposable eye patch according to claim 10, wherein the first and second thicknesses are each in a range of from about 0.1 mm to about 2 mm.

13. The disposable eye patch according to claim 10, wherein the first and second thicknesses are each about 0.5 mm.

14. The disposable eye patch according to claim 10, further comprising a release layer attached to the peripheral portion of the first adhesive layer.

15. The disposable eye patch according to claim 10, wherein at least one of the first sheet member and the second sheet member is made of biocompatible foamed plastic material.

16. The disposable eye patch according to claim 10, wherein the first sheet member and the second sheet member are made of a same material.

17. The disposable eye patch according to claim 10, wherein the first adhesive layer comprises a pressure-sensitive adhesive.

18. The disposable eye patch according to claim 10, further comprising a second adhesive layer between the first adhesive layer and the second sheet member.

19. A method of manufacturing the disposable eye patch of claim 8, comprising:

providing sheet material having an adhesive layer applied to one side of the sheet material;

forming the first sheet member from the sheet material;

forming the second sheet member from the sheet material; and adhering the first sheet member to the second sheet member with the adhesive layer on the first sheet member contacting the adhesive layer on the second sheet member.

20. A method of protecting a patient's eye during treatment of an adjacent portion of the patient's face, comprising adhering a disposable eye patch according to claim 8 over said eye and entirely within a corresponding eye socket of said patient.

21. A dispenser roll assembly, comprising:

an elongate release layer coiled into a roll;

a plurality of disposable eye patches according to claim 10 arranged along the release layer and releasably attached to the release layer by the first adhesive layer.

22. A disposable eye patch comprising:

a first sheet member made of foamed plastic material having a first thickness in a range of from about 0.1 mm to about 5 mm, a second sheet member made of foamed plastic material having a second thickness in a range of from about 0.1 mm to about 5 mm;

a first adhesive layer applied over substantially an entire surface of one side of the first sheet member, the first sheet member being attached to the second sheet member by a central portion of the first adhesive layer, and the second sheet member not overlapping a peripheral portion of the first adhesive layer.

23. The disposable eye patch according to claim 22, wherein the first and second thicknesses are each in a range of from about 0.1 mm to about 2 mm.

24. The disposable eye patch according to claim 22, wherein the first and second thicknesses are each about 0.5 mm.

25. The disposable eye patch according to claim 22, further comprising a release layer attached to the peripheral portion of the first adhesive layer.

26. The disposable eye patch according to claim 22, wherein the first adhesive layer comprises a pressure-sensitive adhesive.

27. The disposable eye patch according to claim 22, further comprising a second adhesive layer between the first adhesive layer and the second sheet member.

28. A method of protecting a patient's eye during treatment of an adjacent portion of the patient's face, comprising adhering a disposable eye patch according to claim 18 over said eye and entirely within a corresponding eye socket of said patient.

29. A dispenser roll assembly, comprising:

an elongate release layer coiled into a roll;

a plurality of disposable eye patches according to claim 22 arranged along the release layer and releasably attached to the release layer by the first adhesive layer.

*30. The disposable eye patch according to claim 22, wherein the peripheral portion extends along an entire periphery of the first adhesive layer, and the second sheet member does not overlap any part of the peripheral portion.*

*31. The disposable eye patch according to claim 10, wherein the peripheral portion extends along an entire periphery of the first adhesive layer, and the second sheet member does not overlap any part of the peripheral portion.*

*32. The disposable eye patch according to claim 10, wherein the second sheet member is smaller than the first sheet member in both vertical and lateral directions.*

*33. The disposable eye patch according to claim 1, wherein the peripheral portion extends along an entire periphery of the first adhesive layer, and the second sheet member does not overlap any part of the peripheral portion.*

*34. The disposable eye patch according to claim 1, wherein the second sheet member is smaller than the first sheet member in both vertical and lateral directions.*

*35. A disposable eye patch for covering a human eye, comprising:*

*a first sheet member sized to fit entirely inside an eye socket in a vertical dimension of the eye socket;*

*a second sheet member smaller than the first sheet member; and*

*a first adhesive layer applied over substantially an entire surface of one side of the first sheet member, the first sheet member being attached to the second sheet member by a central portion of the first adhesive layer, and the second sheet member not overlapping a peripheral portion of the first adhesive layer.*

*36. The disposable eye patch according to claim 35, wherein the peripheral portion extends along an entire periphery of the first adhesive layer, and the second sheet member does not overlap any part of the peripheral portion.*

*37. The disposable eye patch according to claim 35, wherein the second sheet member is smaller than the first sheet member in both vertical and lateral directions.*

*38. A disposable eye patch for covering a human eye, comprising:*

*a first sheet member sized to fit entirely inside an eye socket in a lateral dimension of the eye socket;*

*a second sheet member smaller than the first sheet member; and*

*a first adhesive layer applied over substantially an entire surface of one side of the first sheet member, the first sheet member being attached to the second sheet member by a central portion of the first adhesive layer, and the second sheet member not overlapping a peripheral portion of the first adhesive layer.*

*39. The disposable eye patch according to claim 38, wherein the peripheral portion extends along an entire periphery of the first adhesive layer, and the second sheet member does not overlap any part of the peripheral portion.*

*40. The disposable eye patch according to claim 38, wherein the second sheet member is smaller than the first sheet member in both vertical and lateral directions.*

*41. A disposable eye patch comprising:*

*a first sheet member having a first thickness in a range of from about 0.1 mm to about 5 mm,*

*a second sheet member having a second thickness in a range of from about 0.1 mm to about 5 mm; and*

*a first adhesive layer applied over substantially an entire surface of one side of the first sheet member, the first sheet member being attached to the second sheet member by a central portion of the first adhesive layer, and the second sheet member not overlapping a peripheral portion of the first adhesive layer.*

*42. The disposable eye patch according to claim 41, wherein the first thickness is in a range of from about 0.1 mm to about 2 mm, and the second thickness is in a range of from about 0.1 mm to about 2 mm.*

*43. The disposable eye patch according to claim 41, wherein one of the first sheet member and the second sheet member is made of foamed plastic material.*

*44. The disposable eye patch according to claim 41, wherein the peripheral portion extends along an entire periphery of the first adhesive layer, and the second sheet member does not overlap any part of the peripheral portion.*

*45. A disposable eye patch for covering a human eye, comprising:*

*a sheet member sized to fit entirely inside an eye socket in a lateral dimension of the eye socket and/or in a vertical dimension of the eye socket; and*

*an adhesive layer on at least a portion of a periphery of a surface of the sheet member,*

*a part of the eye patch that contacts most of the eyelid being free of exposed adhesive.*

*46. The disposable eye patch according to claim 45, wherein the sheet member is sized to fit entirely inside the eye socket in both the lateral dimension of the eye socket and the vertical dimension of the eye socket.*

*47. The disposable eye patch according to claim 45, wherein the sheet member comprises biocompatible foamed plastic material.*

*48. The disposable eye patch according to claim 45, wherein the adhesive layer comprises a pressure-sensitive adhesive.*

*49. The disposable eye patch according to claim 45, wherein a width of the sheet member is in a range of from about 20 mm to about 35 mm, and a length of the sheet member is in a range of from about 40 mm to about 60 mm.*

*50. A method of protecting a patient's eye during treatment of an adjacent portion of the patient's face, comprising adhering a disposable eye patch according to claim 45 over said eye and within a corresponding eye socket of said patient.*

*51. A disposable eye patch for covering a human eye, comprising:*

*a sheet member comprising an eye-covering portion sized to fit entirely inside an eye socket in a lateral dimension of the eye socket and/or in a vertical dimension of the eye socket; and*

*an adhesive layer on at least a portion of a periphery of a surface of the sheet member,*

*a part of the eye patch that contacts most of the eyelid being free of exposed adhesive.*

*52. The disposable eye patch according to claim 51, wherein the eye-covering portion is sized to fit entirely inside the eye socket in both the lateral dimension of the eye socket and the vertical dimension of the eye socket.*

*53. The disposable eye patch according to claim 51, wherein a width of the eye-covering portion is in a range of from about 20 mm to about 35 mm, and a length of the eye-covering portion is in a range of from about 40 mm to about 60 mm.*

*54. The disposable eye patch according to claim 51, further comprising a tab provided at an edge of the sheet*

*member, the tab facilitating gripping of the disposable eye patch.*

*55. A method of protecting a patient's eye during treatment of an adjacent portion of the patient's face, comprising adhering a disposable eye patch according to claim 51 over said eye and within a corresponding eye socket of said patient.*

*56. A disposable eye patch for covering a human eye, comprising:*

*a sheet member sized to fit entirely inside an eye socket in at least one dimension of the eye socket; and*

*an adhesive layer on at least a portion of a periphery of a surface of the sheet member,*

*a part of the eye patch that contacts most of the eyelid being free of exposed adhesive.*

*57. The disposable eye patch according to claim 56, wherein the sheet member is sized to fit entirely inside the eye socket in both a lateral dimension of the eye socket and a vertical dimension of the eye socket.*

*58. The disposable eye patch according to claim 56, wherein a width of the sheet member is in a range of from about 20 mm to about 35 mm, and a length of the sheet member is in a range of from about 40 mm to about 60 mm.*

*59. The disposable eye patch according to claim 56, further comprising a tab provided at an edge of the sheet member, the tab facilitating gripping of the disposable eye patch.*

*60. A method of protecting a patient's eye during treatment of an adjacent portion of the patient's face, comprising adhering a disposable eye patch according to claim 56 over said eye and within a corresponding eye socket of said patient.*

* * * * *

UNITED STATES PATENT AND TRADEMARK OFFICE

CERTIFICATE OF CORRECTION

PATENT NO. : RE 39,896 E
APPLICATION NO. : 10/716246
DATED : October 23, 2007
INVENTOR(S) : Nancy L. Arnold et al.

It is certified that error appears in the above-identified patent and that said Letters Patent is hereby corrected as shown below:

In the Claims:

Column 6, line 14, change "claim 8" to --claim 10--;

line 26, change "claim 8" to --claim 10--; and line 65, change "claim 18" to --claim 22--.

Signed and Sealed this

Fifteenth Day of September, 2009

David J. Kappos

David J. Kappos
*Director of the United States Patent and Trademark Office*